US012704685B2

(12) United States Patent
Delianides

(10) Patent No.: US 12,704,685 B2
(45) Date of Patent: Aug. 11, 2026

(54) ELECTRO-OPTICAL PHOTOPLETHYSMOGRAPHIC CONNECTOR

(71) Applicant: Zynex Monitoring Solutions, Inc., Englewood, CO (US)

(72) Inventor: Theodore Philip Delianides, Boulder, CO (US)

(73) Assignee: Zynex Monitoring Solutions, Inc., Englewood, CO (US)

( * ) Notice: Subject to any disclaimer, the term of this patent is extended or adjusted under 35 U.S.C. 154(b) by 200 days.

(21) Appl. No.: 18/644,415

(22) Filed: Apr. 24, 2024

(65) Prior Publication Data

US 2025/0334762 A1 Oct. 30, 2025

(51) Int. Cl.

| | |
|---|---|
| ***G02B 6/38*** | (2006.01) |
| ***A61B 5/1455*** | (2006.01) |
| *A61B 5/024* | (2006.01) |
| *G02B 6/42* | (2006.01) |

(52) U.S. Cl.

CPC ........ *G02B 6/3817* (2013.01); *A61B 5/14551* (2013.01); *A61B 5/14552* (2013.01); *A61B 5/02416* (2013.01); *A61B 2562/222* (2013.01); *A61B 2562/227* (2013.01); *A61B 2562/228* (2013.01); *G02B 6/4298* (2013.01)

(58) Field of Classification Search

CPC .............. G02B 6/3817; A61B 5/02416; A61B 5/02427; A61B 5/02433; A61B 5/1455; A61B 5/14551; A61B 5/14552

See application file for complete search history.

(56) References Cited

U.S. PATENT DOCUMENTS

| | | | |
|---|---|---|---|
| 8,382,666 B1 | 2/2013 | Mao et al. | |
| 10,357,190 B1 | 7/2019 | Mao et al. | |
| 10,405,782 B2 | 9/2019 | Pologe et al. | |
| 2003/0147596 A1* | 8/2003 | Lancelle | G02B 6/382 385/73 |

(Continued)

FOREIGN PATENT DOCUMENTS

WO WO 2012/015734 2/2012

OTHER PUBLICATIONS

EP Search Report for EP App. No. 25167299.4-1113, Dated Aug. 20, 2025. (Note: Applicant believes the references cited on p. 2 are the correctly cited references and the references cited on p. 4 are incorrectly cited. Nonetheless, all references cited are included herein.).

*Primary Examiner* — Michael Stahl
(74) *Attorney, Agent, or Firm* — Remenick PLLC

(57) ABSTRACT

A photoplethysmographic device has a monitor with a monitor connector and a patient cable. The patient cable has a patient cable connector, a cable, and a sensor. The monitor connector and the patient cable connector each have an electrical portion with two or more electrical connections and an optical portion with two or more optical connections. The monitor connector and the patient cable connector are removably couplable to each other. The optical connections of the optical portions of the monitor connector and the patient cable connector are physical contact connections. At least one of the optical portions of either the monitor connector or the patient cable connector is movably positioned within the associated monitor connector or patient cable connector.

14 Claims, 4 Drawing Sheets

(56) References Cited

U.S. PATENT DOCUMENTS

| | | | | |
|---|---|---|---|---|
| 2003/0181796 | A1 | 9/2003 | Pologe | |
| 2004/0131317 | A1 | 7/2004 | Grzegorzewska et al. | |
| 2006/0098921 | A1* | 5/2006 | Benaron | H01R 24/58 385/75 |
| 2009/0028495 | A1* | 1/2009 | Anrig | G02B 6/3813 385/59 |
| 2010/0310213 | A1 | 12/2010 | Lewallen et al. | |
| 2014/0135601 | A1* | 5/2014 | Pologe | A61B 5/14546 600/324 |
| 2015/0110444 | A1* | 4/2015 | Tanaka | G02B 6/3817 385/75 |
| 2016/0077287 | A1* | 3/2016 | Isenhour | G02B 6/3825 385/76 |
| 2018/0103877 | A1 | 4/2018 | Pologe et al. | |
| 2021/0356678 | A1 | 11/2021 | Bretz et al. | |

* cited by examiner

ELECTRO-OPTICAL PHOTOPLETHYSMOGRAPHIC CONNECTOR

RIGHTS IN THE INVENTION

This invention was made with government support under R44 HL073518 awarded by the National Institutes of Health. The government has certain rights in the invention.

FIELD OF THE INVENTION

This invention is in the field of photoplethysmography.

BACKGROUND OF THE INVENTION

In the science of photoplethysmography, light is used to illuminate or trans-illuminate living tissue for the purpose of providing noninvasive measurements of blood analytes including but not limited to the levels of arterial oxyhemoglobin, carboxyhemoglobin, methemoglobin, reduced hemoglobin, and/or total hemoglobin. Additionally, photoplethysmography can be designed to measure various hemodynamic parameters, and/or tissue properties including, but not limited to, heart rate, respiratory rate, and perfusion.

In this monitoring modality multiple different spectral bands of light are directed into living tissue (the "tissue-under-test") and a portion of the light that is not absorbed by the tissue or scattered in some other direction is detected a short distance from the point at which the light entered the tissue. When light, at wavelengths that can be absorbed by hemoglobin or other components of arterial blood, passes through living tissue the light is modulated by the pulsatile arterial blood flow. The pulsatile (or photoplethysmographic) light signals exiting the tissue and picked up by the detector are converted into electronic signals (or photoplethysmographic signals or photoplethysmographic data) by a photodetector and are then used to calculate the desired blood analyte levels and/or hemodynamic parameters. A device which generates light to be emitted into the tissue and detects and processes the photoplethysmographic signals (or data) emitted by the tissue, to measure the levels of various blood analytes and/or various hemodynamic parameters, is a photoplethysmographic device. A photoplethysmographic device typically includes a photoplethysmographic monitor combined with a sensor. The first widely used commercial photoplethysmographic device was a pulse oximeter, a photoplethysmographic device designed to noninvasively measure, at least, arterial blood oxygen saturation. This device is now used in almost all areas of medicine.

The (photoplethysmographic) monitor includes electronic circuitry for controlling light emitters that emit light which is then incident on the tissue. The monitor also performs the functions of receiving and processing the photoplethysmographic signals emitted from the tissue, converting these photoplethysmographic data into the various blood analytes and/or hemodynamic parameter measurements, and displaying these measurements on some form of user display. Also included in any photoplethysmographic device is a sensor which is affixed to, or held in place against, the tissue to deliver light from the emitters to the tissue. The sensor further includes a photodetector for receiving the photoplethysmographic signals from the tissue.

Typically, the sensor is connected to the monitor by a patient cable that has a connector to allow it to be removably connected to the monitor. Further, depending on the design of the patient cable, the sensor can be permanently connected to the distal end of patient cable, or the patient cable may have a connector on its distal end to connect and disconnect to the sensors.

In the first commercial pulse oximeter the light directed into the tissue was generated by a tungsten lamp and conducted to the sensor by a light guide, in this case a fiber optic bundle. A second fiber optic light guide, also connected to the sensor, picked up a small portion of the light emitted from the tissue and delivered that light back to the monitor, where the received light was split into two paths and passed through two separate interference filters, to generate two separate spectral bands of light, and finally to two separate photodetectors. The photodetectors converted the received optical photoplethysmographic signals to electronic photoplethysmographic signals for processing into measurements of oxygen saturation. The patient cable in this pulse oximeter was quite bulky in order to handle two separate large diameter fiber optic bundles.

This system worked but was limited to working with only two spectral bands of light and the optics of the system were bulky and inefficient, resulting in very low received light levels making it difficult, if not impossible, to make readings on thicker tissue (e.g. thicker fingers) or on tissue with a high melanin content. Further this device was limited to the measurement of only a single blood analyte, an estimate of arterial oxygen saturation.

In later pulse oximeters the broadband tungsten light source was replaced with two light emitting diodes (LEDs). One LED had a center wavelength around 660 nanometers (nm), in the red portion of the visible spectrum, and a second LED had a center wavelength typically around 900 nm or 940 nm, in the near infrared region. These diodes were typically positioned directly in the sensor within a few millimeters from the tissue they illuminated, generating a strong optical signal for probing the tissue. The photodetector was also positioned directly in the sensor eliminating the need for fiber optic bundles in the patient cable as now it was only an electrical cable.

This worked well on almost all tissue and made the pulse oximeter into a nearly universally used monitoring device in healthcare. However, using LEDs for photoplethysmographic measurement still came with some limitations. The spectral content of LEDs, while centered at the required wavelengths, is very broad, typically about 100 nm. These broadband light sources limit the measurement accuracy that can be attained by these LED-based pulse oximeters, and they also limit the number of blood analytes that can be measured.

To make it possible to accurately measure multiple blood analytes, multiple different spectral bands of light are required, and the full power spectral bandwidth of (at least some of) these spectral bands should be as close to monochromatic as possible. These optical requirements can be met by replacing the LED light sources (or at least some of the LED light sources) for photoplethysmographic measurement to lasers and in particular semiconductor, or diode lasers, which have a spectral bandpass in the 1 nm range. This is nearly monochromatic compared to LED emitters.

The use of lasers in photoplethysmography, however, also presents certain challenges. If lasers are to be used in a photoplethysmographic device, and if those lasers are to be positioned somewhere other than integral to the sensor, then the light generated by the lasers must be communicated, or transmitted, to the sensor. This communication will typically further require the use of a connector located somewhere between the monitor and the sensor to communicate the light emitted by the lasers to the tissue as well as to communicate the photoplethysmographic data (which may be electronic data) received by the sensor back to the monitor. Therefore, there is a need for a hybrid electro-optical connector for a photoplethysmographic device that, ideally, can communicate multiple optical and electrical signals and which can do so at a low cost and with low optical losses. Fortunately, light from a diode laser can be coupled into a single fiber for the purpose of photoplethysmographic measurements, eliminating the need for large diameter fiber optic bundles.

SUMMARY OF THE INVENTION

The present invention overcomes the problems and disadvantages associated with current strategies and designs and provides new systems and methods of manufacturing photoplethysmographic devices.

One embodiment of the invention is directed to a photoplethysmographic device. The device has a monitor with a monitor connector and a patient cable. The patient cable has a patient cable connector, a cable, and a sensor. The monitor connector and the patient cable connector each have an electrical portion with two or more electrical connections and an optical portion with two or more optical connections. The monitor connector and the patient cable connector are removably couplable to each other. The optical connections of the optical portions of the monitor connector and the patient cable connector are physical contact connections. At least one of the optical portions of either the monitor connector or the patient cable connector is movably positioned within the associated monitor connector or patient cable connector.

Preferably, the optical portions of the monitor connector and patient cable connector together include one or more mating pairs of pins and holes. In a preferred embodiment, the monitor connector has a first portion of a latching mechanism and the patient cable connector has a second portion of the latching mechanism. At least one of the optical portions of either the monitor connector or the patient cable connector preferably includes a backing spring that biases an associated optical portion proud of an associated connector end face. Preferably, the latching mechanism has a retaining force greater than a force of the backing spring driving the monitor connector and the patient cable connector apart when they are in a mated position. At least one optical fiber from the optical connections preferably runs through the backing spring. Preferably, the optical portions are adapted to transmit one or more laser signals from the monitor to the sensor and the electrical portions are adapted to transmit electrical data between the monitor and the sensor.

Another embodiment of the invention is directed to a method of assembling a monitor connector and a patient cable connector pair for a photoplethysmographic device. The method includes the steps of, for the monitor connector: positioning an electrical portion within a monitor connector housing, inserting two or more electrical connections into the electrical portion, positioning an optical portion within the monitor connector housing, inserting two or more optical connections into the optical portion, and coupling the monitor connector to a photoplethysmographic monitor. The method also includes the steps of, for the patient cable connector: positioning an electrical portion within a patient cable connector housing, inserting two or more electrical connections into the electrical portion, positioning an optical portion within the patient cable connector housing, inserting two or more optical connections into the optical portion, and coupling the patient cable connector to a sensor. The monitor connector and the patient cable connector are removably couplable to each other. The optical connections of the optical portions of the monitor connector and the patient cable connector are physical-contact connections. At least one of the optical portions of either the monitor connector or the patient cable connector is movably positioned within the associated monitor connector or patient cable connector.

Preferably, the method further comprises the step including one or more mating pairs of alignment pins and alignment holes in the pair of optical portions of the monitor connector and the patient cable connector. The method preferably further comprises the steps of connecting a first portion of a latching mechanism to one side of the connector pair and connecting a second portion of a latching mechanism to the other side of the connector pair. The method preferably further comprises the step of coupling a backing spring to at least one of the optical portions of either the monitor connector or the patient cable connector. In a preferred embodiment, the latching mechanism provides a retaining force greater than a force of the backing spring driving the monitor connector and the patient cable connector apart when they are in the mated position. The method preferably further comprises the step of positioning at least one optical fiber from the optical portion through the backing spring. The optical portions are preferably adapted to transmit one or more laser signals from the monitor to the sensor and the electrical portions are adapted to transmit electrical data between the monitor and the sensor.

Other embodiments and advantages of the invention are set forth in part in the description, which follows, and in part, may be obvious from this description, or may be learned from the practice of the invention.

BRIEF DESCRIPTION OF THE DRAWINGS

The foregoing features of embodiments will be more readily understood by reference to the following detailed description, taken with reference to the accompanying drawings, which show.

DETAILED DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Figure 1:
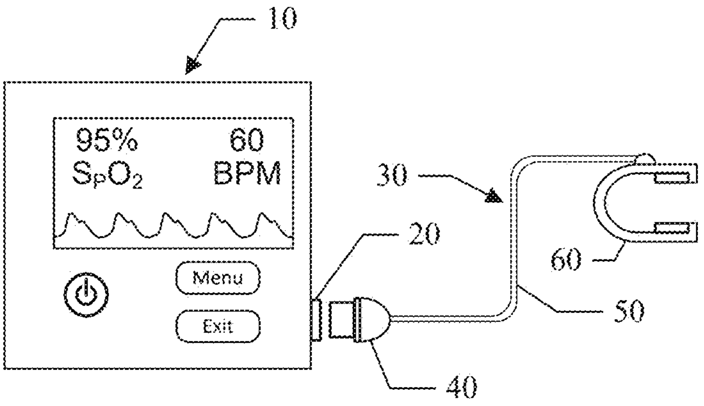
FIG. 1: Photoplethysmographic device with monitor, patient cable, and sensor.

Photoplethysmographic devices, such as that shown schematically in FIG. 1, come in many forms including, but not limited to: a standalone monitor 10 having a built-in display and detachable sensor 60, or photoplethysmographic devices that transmit the measurements for display to a remote display, or an attached computer, or by another display device such as a smart phone.

The photoplethysmographic monitor 10 may also provide other functions and include other components such as a keypad, buttons, or touchscreen for user input, visible indicators (e.g. LED lights), audible enunciators (e.g. speakers)

for alarms, and/or wired or wireless connection ports (e.g. USB, RS232, Ethernet, Bluetooth) for digital and analog inputs and outputs.

The photoplethysmographic device shown in FIG. 1 includes a photoplethysmographic monitor 10, with display and various controls for operating monitor 10, patient cable 30, and sensor 60. Monitor connector 20, is designed to connect, or mate, to patient cable connector 40 to pass signals from the monitor 10 to sensor 60 and to pass signals from sensor 60 to monitor 10. Patient cable 30 in FIG. 1 includes patient cable connector 40, cable 50, and sensor 60. In some embodiments, an additional connector may exist between cable 50 and sensor 60, to allow cable 50 to remain connected to monitor 10 while sensor 60 is swapped out for an alternate sensor. In some embodiments, patient cable 30 may be hardwired or fixed to monitor connector 10 and connector pair 20 and 40 may be positioned between cable 50 and sensor 60.

The photoplethysmographic device shown in FIG. 1 includes at least one laser, typically a diode laser, that is used to generate light, that is transmitted to sensor 60, to probe the tissue-under-test in the sensor. These laser(s) are typically positioned at a distance from sensor 60. Thus, light from the laser(s) would be transmitted by a light guide, typically an optical fiber located within the cable 50, from the laser to the sensor 60. In some embodiments, the laser(s) are housed within monitor 10, but in alternate embodiments the lasers could be located in other places, for example in a housing some distance from monitor 10 and connected to monitor 10 by a cable or by a wireless connection.

Regardless of the exact location of the laser(s), it is desirable to be able to separate the connection between the sensor and the laser(s). In the embodiment shown in FIG. 1, the laser(s) reside in monitor 10 and the separable connection is at monitor connector 20. Thus, monitor connector 20 and patient cable connector 40 allow patient cable 30 to be removably couplable, or connected and disconnected from monitor 10. This allows for different types of sensors to be used on different patients or on different locations on a given patient. For example, an ear sensor may be more appropriate on one patient and a finger sensor on another. Monitor connector 20 and patient cable connector 40 must therefore be able to pass the optical signals from the laser(s) and the electrical signals from monitor 10 and/or sensor 60. Such a connector preferably requires a precisely aligned optical connection, to minimize optical transmission losses, and considerably less precisely aligned electrical connections, which only require contact between any portion of the two sides of the connector pin and socket (or similar mating elements) to conduct signals. The alignment described herein is specifically referring to lateral, axial, and angular alignment between the optical fiber end faces of monitor connector 20 and patient cable connector 40.

Figure 2:
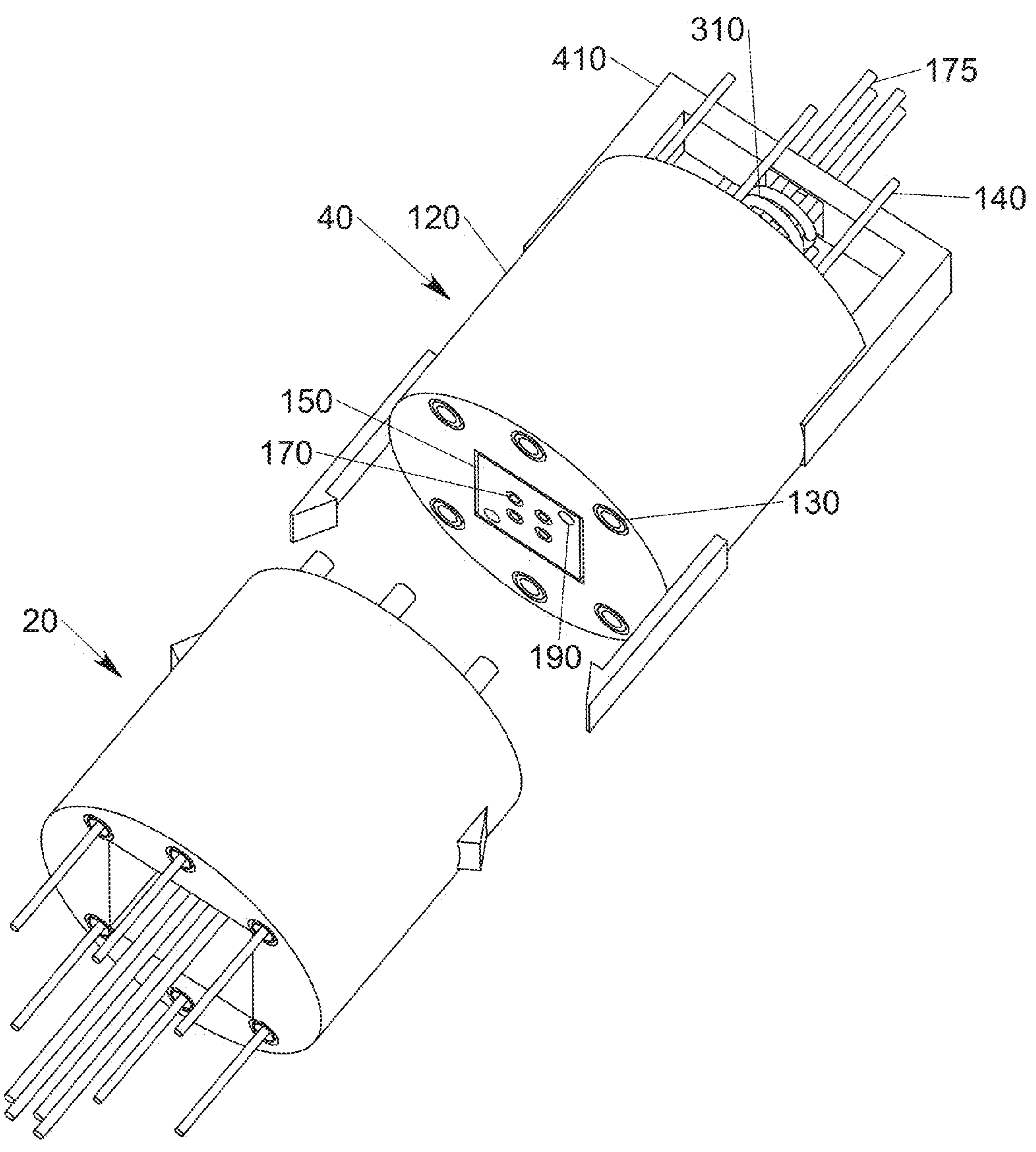
FIG. 2: Patient cable connector, detailed view.

FIG. 2 shows a detailed view of the patient cable connector 40 adjacent to monitor connector 20. Connector 40 includes an electrical portion 120 and an optical portion 150 that, in this embodiment, resides within electrical portion 120. Electrical portion 120 houses a plurality of electrical sockets 130. In this drawing six individual sockets are shown but the connectors may have more or fewer electrical connections (electrical pin and socket pairs). Each electrical socket 130 is typically connected to a wire 140 and these wires 140 are routed through cable 50 (shown in FIG. 1).

Optical portion 150 of connector 40 further includes optical fiber end faces 170. Each optical fiber 175 in optical portion 150 provides for an optical connection. As shown in FIG. 2, there are four optical fibers 175 terminating in optical fiber end faces 170 at the surface of optical portion 150. More or fewer optical connections can be included in connectors 20 and 40 as required. Terminating the end faces 170 of optical fibers 175 typically includes a polishing operation to ensure that the mating face of optical portion 150 is extremely flat and the fiber end faces 170 are as free of scratches or blemishes as possible to minimize optical coupling losses when the two sides of the connector pair (20 and 40) are mated. Additionally, optical portion 150 also includes alignment (or registrations) holes 190. In this case the two alignment holes 190 are positioned diagonally across from each other in the optical portion 150. More or fewer alignment holes can be included in connectors 20 and 40 as required.

FIG. 2 also shows spring retainer 410 and backing spring 310, which drive (or bias) the movably positioned optical portion 150 of patient cable connector 40 toward monitor connector 20 so that when the two sides of the connector pair are mated there will be pressure between the two optical portions, or at least between the optical fiber end faces 170 and 270 (shown in FIG. 3), of the connectors to provide abutting, face-to-face contact between the fiber end faces 170 and 270. Spring retainer 410 snaps into, or is otherwise affixed to, patient cable connector 40 to provide a preload to backing spring 310 to ensure that backing spring 310 is slightly compressed even when the two sides of the connector are not in the mated position. Physical contact optical connections are preferably low optical loss connections that also provide a low level of back reflection. The loss is expected to be less than 1 dB, 0.5 dB, or 0.25 dB.

Figure 3:
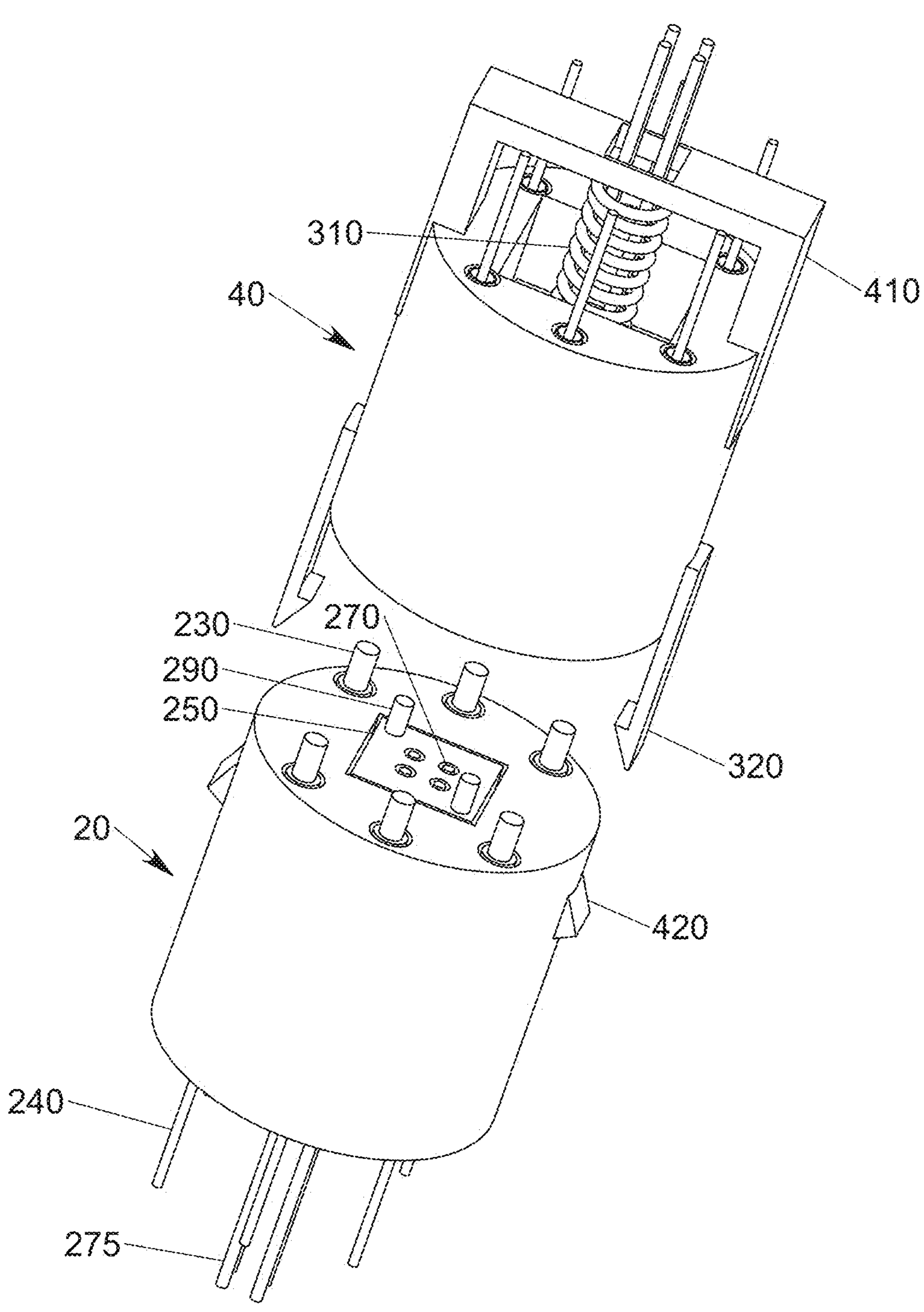
FIG. 3: Monitor connector, detailed view.

FIG. 3 shows a detailed view of monitor connector 20. The end face of monitor connector 20 shows the mating electrical pins 230 that mate with electrical sockets 130 (shown in FIG. 2). Also shown in the optical portion 250 of patient cable connector 20 are the fiber end faces 270 and alignment pins 290 that insert into alignment holes 190 (shown in FIG. 2). These mating pairs of pins and holes ensure highly precise alignment of the optical portions 250 and 150 of the two sides of the connector pair 20 and 40. Electrical pins 230 connect to wires 240 and fiber end faces 270 are the polished end faces of fibers 275.

FIG. 3 also shows catch 420 on monitor connector 20 and latch 320 on patient cable connector 40, which form the first and second portions of the latching mechanism for this connector pair 20 and 40. Latch 320 rides up and over catch 420 as patient cable connector 40 is mated with monitor connector 20 to hold the two sides of the connector together, which would otherwise be forced apart by the restoring force of backing spring 310 pushing against the optical portion 150 and the spring retainer 410.

Figure 4:
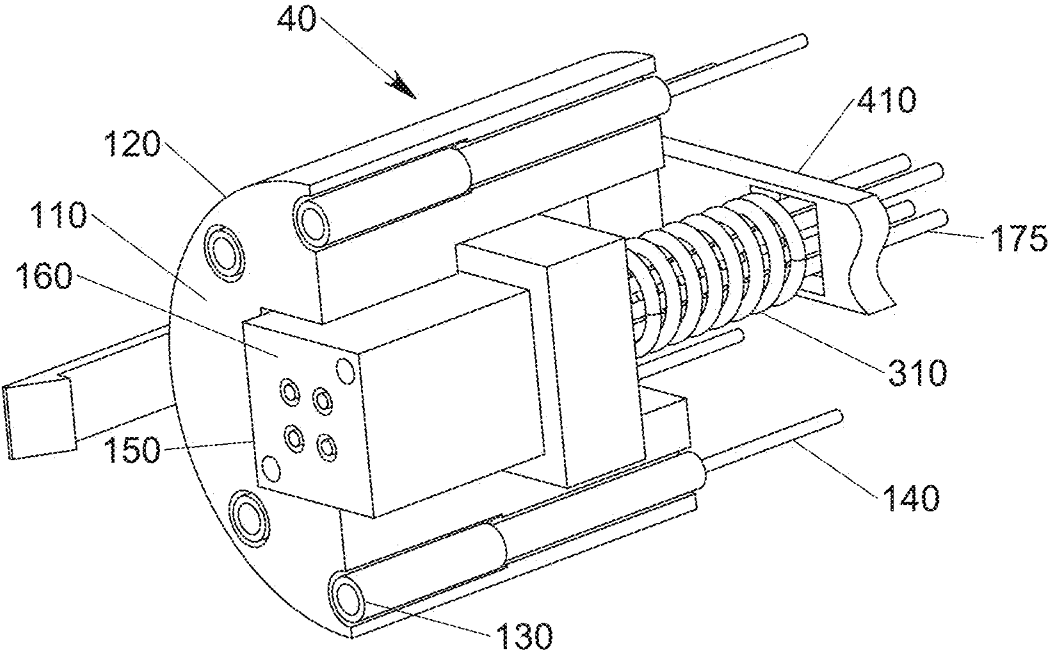
FIG. 4: Patient cable connector, cutaway side view.

FIG. 4 is a cutaway side view of patient cable connector 40. This view shows backing spring 310 driving (or biasing) the movably positioned optical portion 150 proud of patient cable connector end face 110. When patient cable connector 40 is mated with monitor connector 20, optical portion 150 is driven back into patient cable connector 40 until optical portion end face 160 becomes approximately coplanar with patient cable connector end face 110. Backing spring 310 maintains a forward force on optical portion 150 to ensure good physical contact between fiber end face 170 of the patient cable connector 40 and fiber end face 270 of the monitor connector 20. In some embodiments, backing spring 310, spring retainer 410, and movable optical portion 150 may be positioned in monitor connector 20. In some embodiments, both monitor connector 20 and patient cable connector 40 may have an associated backing spring, spring retainer, and a movable optical portion.

Fibers 175 preferably run through backing spring 310. This allows backing spring 310 to provide more uniform pressure across optical portion end face 160 while still maintaining an overall miniature connector design.

In some embodiments, the electrical pins 230 (FIG. 3) and electrical sockets 130 (FIG. 2) can be positioned in the opposite way with electrical sockets 130 in monitor connector 20 and electrical pins 230 in patient cable connector 40. Similarly, the position of alignment holes 190 (FIG. 2) and alignment pins 290 (FIG. 3) can be swapped. As can catch 420 (FIG. 3) and latch 320 (FIG. 3).

Catch 420 and latch 320 can take any one of a number of different forms including, for example, a screw connection between the two sides of the connector or a ball and detent arrangement. Regardless of the form of the latching mechanism, catch 420 and latch 320 preferably provide a retaining force between the monitor connector 20 and patient cable connector 40 that is sufficient to overcome the separation force of backing spring 310 driving optical portions 150 and 250 of the two sides of the connector (20 and 40) apart when the two sides of the connector (20 and 40) are in the mated position.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A photoplethysmographic device comprising:

a monitor with a monitor connector;

a patient cable, the patient cable comprising a patient cable connector, a cable, and a sensor;

the monitor connector and the patient cable connector each comprising an electrical portion with two or more electrical connections and an optical portion with two or more optical connections;

wherein the monitor connector and the patient cable connector are removably couplable to each other;

wherein the optical connections of the optical portions of the monitor connector and the patient cable connector are physical contact connections; and at least one of the optical portions of either the monitor connector or the patient cable connector is movably positioned within the associated monitor connector or patient cable connector.

2. The device of claim 1, wherein the optical portions of the monitor connector and patient cable connector together include one or more mating pairs of pins and holes.

3. The device of claim 1, wherein the monitor connector has a first portion of a latching mechanism and the patient cable connector has a second portion of the latching mechanism.

4. The device of claim 3, wherein at least one of the optical portions of either the monitor connector or the patient cable connector includes a backing spring that biases an associated optical portion proud of an associated connector end face.

5. The device of claim 4, wherein the latching mechanism has a retaining force greater than a force of the backing spring driving the monitor connector and the patient cable connector apart when they are in a mated position.

6. The device of claim 4, wherein at least one optical fiber from the optical connections runs through the backing spring.

7. The device of claim 1, wherein the optical portions are adapted to transmit one or more laser signals from the monitor to the sensor and the electrical portions are adapted to transmit electrical data between the monitor and the sensor.

8. A method of assembling a monitor connector and a patient cable connector pair for a photoplethysmographic device, comprising the steps of:

for the monitor connector:

positioning an electrical portion within a monitor connector housing;

inserting two or more electrical connections into the electrical portion;

positioning an optical portion within the monitor connector housing;

inserting two or more optical connections into the optical portion;

coupling the monitor connector to a photoplethysmographic monitor;

for the patient cable connector:

positioning an electrical portion within a patient cable connector housing;

inserting two or more electrical connections into the electrical portion;

positioning an optical portion within the patient cable connector housing;

inserting two or more optical connections into the optical portion;

coupling the patient cable connector to a sensor;

wherein the monitor connector and the patient cable connector are removably couplable to each other;

wherein the optical connections of the optical portions of the monitor connector and the patient cable connector are physical-contact connections; and at least one of the optical portions of either the monitor connector or the patient cable connector is movably positioned within the associated monitor connector or patient cable connector.

9. The method of claim 8, further comprising the step including one or more mating pairs of alignment pins and alignment holes in the pair of optical portions of the monitor connector and the patient cable connector.

10. The method of claim 8, further comprising the steps of connecting a first portion of a latching mechanism to one side of the connector pair and connecting a second portion of a latching mechanism to the other side of the connector pair.

11. The method of claim 10, further comprising the step of coupling a backing spring to at least one of the optical portions of either the monitor connector or the patient cable connector.

12. The method of claim 11, wherein the latching mechanism provides a retaining force greater than a force of the backing spring driving the monitor connector and the patient cable connector apart when they are in the mated position.

13. The method of claim 11, further comprising the step of positioning at least one optical fiber from the optical portion through the backing spring.

14. The method of claim 8, wherein the optical portions are adapted to transmit one or more laser signals from the monitor to the sensor and the electrical portions are adapted to transmit electrical data between the monitor and the sensor.

* * * * *